US006569616B1

(12) United States Patent
Compton et al.

(10) Patent No.: US 6,569,616 B1
(45) Date of Patent: May 27, 2003

(54) HUMAN CYTOMEGALOVIRUS GLYCOPROTEIN O AS A NEW DRUG TARGET AND SUBUNIT VACCINE CANDIDATE

(75) Inventors: Teresa Compton, Madison, WI (US); Mary T. Huber, Portland, OR (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/627,986

(22) Filed: Jul. 28, 2000

Related U.S. Application Data

(60) Provisional application No. 60/146,180, filed on Jul. 29, 1999.

(51) Int. Cl.[7] .......................... C12Q 1/70; A61K 39/00
(52) U.S. Cl. ..................... 435/5; 424/184.1; 424/230.1; 424/229.1
(58) Field of Search .................. 424/184.1, 230.1, 424/229.1; 435/5

(56) References Cited

U.S. PATENT DOCUMENTS

| | | | |
|---|---|---|---|
| 5,011,829 A | * 4/1991 | Hirsch et al. | 514/50 |
| 5,149,529 A | 9/1992 | Ho et al. | 424/88 |
| 5,171,568 A | 12/1992 | Burke et al. | 424/89 |
| 5,244,792 A | 9/1993 | Burke et al. | 435/69.3 |
| 5,477,039 A | 12/1995 | Lisimaque et al. | 235/380 |
| 5,612,041 A | 3/1997 | Burke et al. | 424/231 |
| 5,648,079 A | 7/1997 | Burke et al. | 424/186.1 |
| 5,750,106 A | 5/1998 | Ostberg | 424/142.1 |
| 5,750,114 A | 5/1998 | Burke et al. | 424/231.1 |
| 5,759,814 A | 6/1998 | Burke et al. | 435/69.3 |
| 5,763,161 A | 6/1998 | Kurihara et al. | 435/5 |
| 5,795,579 A | 8/1998 | Burke et al. | 424/231.1 |
| 5,800,981 A | 9/1998 | Bruggeman et al. | 435/5 |
| 5,807,557 A | 9/1998 | Dubin | 424/231.1 |
| 5,837,261 A | 11/1998 | Inglis et al. | 424/229.1 |
| 5,853,734 A | 12/1998 | Chang et al. | 424/194.1 |

OTHER PUBLICATIONS

Pietropaolo, R., Direct Interaction between Human Cytomegalovirus Glycoprotein B and Cellular Annexin II, Journal of Virology vol. 71, No. 12, 1997, pp. 9803–9807.*
Huber, Mary T. et al., The HCMV UL74 Gene Encodes the Third Component of the gH/gL Complex (abstract). Aug. 1998.
Boyle, Kathleen A., et al., Glycoprotein B of Human Cytomegalovirus Elicts Intracellular Signaling (abstract). Aug. 1998.
Huber, Mary T. et al., Characterization of a Novel Third Member of the Human Cytomegalovirus Glycoprotein H–Glycoprotein L Complex, J. of Virology, V.71, N. 7, Jul. 1997, p. 5391–5398.
Huber, Mary T. et al., Intracellular Formation and Processing of the Heterotrimeric gH–gL–gO (gCIII) Glycoprotein Envelope Complex of Human Cytomegalovirus, J. of Virology, V. 73, N. 5, May 1999, p. 3886–3892.
Huber, Mary T. et al., The Human Cytomegalovirus UL74 Gene Encodes the Third Component of the Glycoprotein H–Glycoprotein L–Containing Envelope Complex, J. of Virology, V. 72, N.10, Oct. 1998, p. 8191–8197.

* cited by examiner

*Primary Examiner*—Hankyel T. Park
*Assistant Examiner*—Stacy S. Brown
(74) *Attorney, Agent, or Firm*—Quarles & Brady LLP

(57) ABSTRACT

A method of designing a new anti-CMV drug is disclosed. In one embodiment, the invention comprises (a) analyzing the binding of glycoprotein O to a glycoprotein O receptor and (b) designing a candidate drug that would competitively interfere with glycoprotein O binding to glycoprotein O receptor and (c) showing that the candidate drug competitively inhibits glycoprotein O binding to glycoprotein O receptor. A method of screening anti-CMV drugs, a vaccine effective to diminish CMV infection, and a method of diminishing CMV infection are also disclosed.

3 Claims, 2 Drawing Sheets

MGRKEMMVRDVPKMFVLISISFLLVSFINCKVMSKALYNRPWRGLVLSKIGKYKLDQLKLEILRQLETTIST
KYNVSKQPVKNLTMNTEFPQYYILAGPIQNYSITYLWFDFYSTQLRKPAKYVYSQYNHTAKTITFRPPPCGR
VPSMTCLSEMLNVSKRNDTGEQGCGNFTFNPMFFNVPRWNTKLYVGPTKVNVDSQTIYFLGLTALLLRY
AQRNCTHSFYLVNAMSRNLFRVPKYINGTKLKNTMRKLRKQAPVKEQFEKKAKKTQSTTPYFSYTSA
ALNVITNVTYSITTAARRVSTSTIAYRPDSSFMKSIMATQLRDLATWVYTLRYRQNPFCEPSRNRTAVSEF
MKNTHVLIRNETPYTIYGTLDMSSLYYNETMFVENKTASDSNKTTPTSPSMGFQRTFIDPLWDYLDSLLFL
DEIRNFSLRSPTYVNLTPPEHRRAVNLSTSNSLWWWLQ

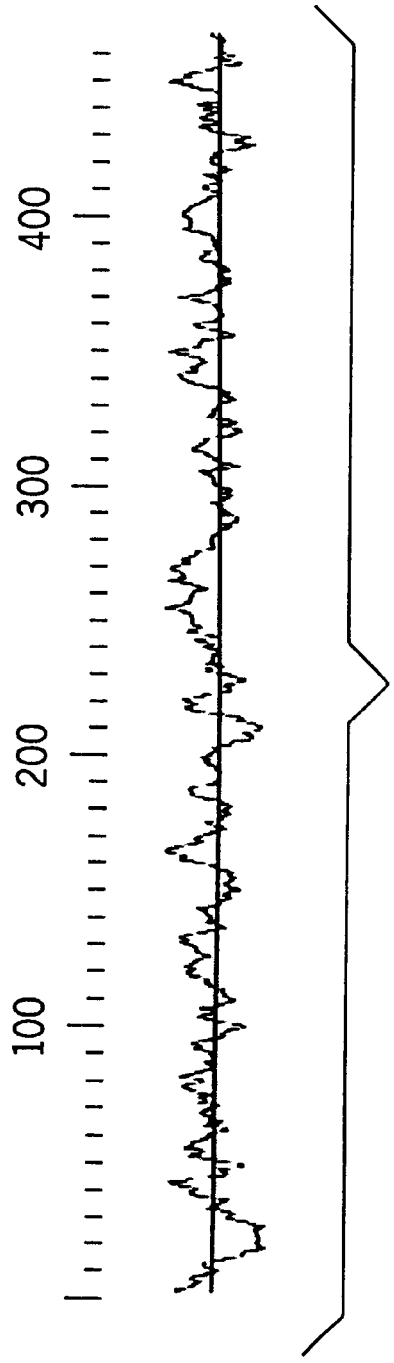

FIG. 3

HUMAN CYTOMEGALOVIRUS GLYCOPROTEIN O AS A NEW DRUG TARGET AND SUBUNIT VACCINE CANDIDATE

CROSS-REFERENCE TO RELATED APPLICATION

This application claims priority to U.S. provisional application Ser. No. 60/146,180, filed Jul. 29, 1999. Ser. No. 60/146,180 is incorporated by reference herein.

STATEMENT REGARDING FEDERALLY SPONSORED RESEARCH AND DEVELOPMENT

This invention was made with United States government support awarded by the following agencies: NIH A134998. The United States has certain rights in this invention.

BACKGROUND OF THE INVENTION

For viruses such as the herpes viruses, which contain a cell-derived lipid envelope, the virally-encoded envelope proteins are the primary determinants of tissue tropism and the mediators of virus entry, cell to cell spread and maturation of virus particles. Human cytomegalovirus (CMV), a member of the Herpesviridae family, is a significant opportunistic pathogen responsible for serious clinical consequences in a variety of immunosuppressed patient groups such as neonate and infants, persons with AIDS and individuals undergoing immunosuppressive regimes for the purpose of organ or bone marrow transplantation. As is true for other human herpes viruses, CMV establishes a life-long latent infection with its human host and is ubiquitous in the population with upwards of 75% infectivity rate found in the United States. At present there is no protective vaccine. Currently available antiviral drugs which target viral DNA replication are efficacious but exhibit significant host toxicity and a high spontaneous resistance rate. Thus, there is a tremendous need to identify alternative drug targets and immunogens that elicit protective immunity.

BRIEF SUMMARY OF THE INVENTION

In one embodiment, the present invention is a method of designing a new anti-CMV drug comprising (a) analyzing the binding of glycoprotein O to a glycoprotein O receptor and (b) designing a candidate drug that would competitively interfere with glycoprotein O binding to glycoprotein O receptor and (c) showing that the candidate drug competitively inhibits glycoprotein O binding to glycoprotein O receptor.

In a preferred embodiment, the candidate drug is a peptide or other compound that effectively interferes with gO function.

In another embodiment, the present invention is a method of screening anti-CMV drugs comprising the step of determining whether a candidate drug interferes with glycoprotein O-containing complex binding to a cell surface.

In another embodiment, the present invention is a vaccine effective to diminish CMV infection comprising at least a fragment of glycoprotein O polypeptide, preferably in combination with a pharmacologically acceptable carrier.

In another embodiment, the present invention is an anti-CMV drug comprising of at least a fragment of CMV glycoprotein O and a pharmacologically acceptable carrier.

In another embodiment, the present invention is a method of diminishing CMV infection comprising the step of introducing anti-CMV glycoprotein O antibodies into a CMV-infected subject.

It is an object of the present invention to design or screen anti-CMV drugs.

It is another object of the present invention to diminish CMV infection.

It is yet another object of the present invention to provide new anti-CMV drugs, vaccines and antibodies.

Other objects, features and advantages of the present invention will become apparent to one of skill in the art after review of the specification, claims and drawings.

BRIEF DESCRIPTION OF THE DRAWINGS

FIG. 3 is the predicted amino acid sequence of gO. The predicted signal/anchor domain is in bold, and potential N-glycosylation sites are underlined. Kyte-Doolittle hydropathy analysis is shown at the bottom.

DETAILED DESCRIPTION OF THE INVENTION

A. In General

Discovery of Glycoprotein O.

One envelope complex of CMV known to be required for entry of the virus is the glycoprotein H (gH)-containing complex. Homologs of gH are found in all herpes viruses and are generally complexed with a second gene product, glycoprotein L (gL). We initially attempted to reconstitute the gH complex of CMV from recombinant sources by co-expression of gH and gL in a baculovirus system. However, these efforts were unsuccessful. Using antibodies specific for gH, we found that the gH complex of CMV likely contained a third viral component (Huber, M. T. and T. Compton, *J. Virol.* 71:5391–8, 1997). The genome of a laboratory strain of CMV is completely deduced (Chee, M. S., et al., *Curr. Top. Microbiol. Immunol.* 154(125):125–69, 1990), and analysis of open reading frames encoded in the genome revealed that as many as 55 of the 208 genes of CMV potentially encode envelope glycoproteins. To date, however, only 5 genes are linked to defined envelope protein components.

To determine which gene may encode the third gH-complex component, we subjected a preparation of purified protein to microsequence analysis. Our analysis of the results of the protein sequence allowed us to identify this protein as the product of a particular gene (UL74), one of the predicted envelope glycoproteins. We designated the UL74 gene product as glycoprotein O (gO) (Huber, M. T. and T. Compton, *J. Virol.* 72:8191–97, 1998).

Potential Function of gO.

To determine whether gO was important in the lifecycle of CMV, we produced a high-titer antiserum. This antiserum is monospecific for gO and is capable of precipitating gO and its complexing partners, gH and gL (Huber, M. T. and T. Compton, supra, 1998) in CMV-infected cells (Huber, M. T. and T. Compton, supra, 1998; Huber, M. T. and T. Compton, *J. Virol.* 73:3886–92, 1999). We then determined whether anti-gO antibodies had any viral neutralizing activity by measuring the effect of incubation of this serum with CMV particles on virus entry. To this end, we have developed a sensitive virus entry assay (Pietropaolo, R. and T. Compton, *J. Virol.* 71:9803–7,1997). This assay measures the synthesis of the major immediate early protein of CMV, the first viral gene to be expressed in infected cells after successful delivery of the genome. In our experiments, CMV viral preparations were incubated with increasing concentrations of purified anti-gO serum or with non-immune serum or an antibody to the gH protein. We observed a dose-dependent inhibition of CMV infection in the presence of the anti-gO serum whereas no inhibition was observed with the preimmune or anti-gH monoclonal antibody. The blocking activity of the anti-gO antiserum strongly suggests that (a) gO is needed for viral entry and (b) antibodies reactive with gO may be protective against infection.

Figure 1:
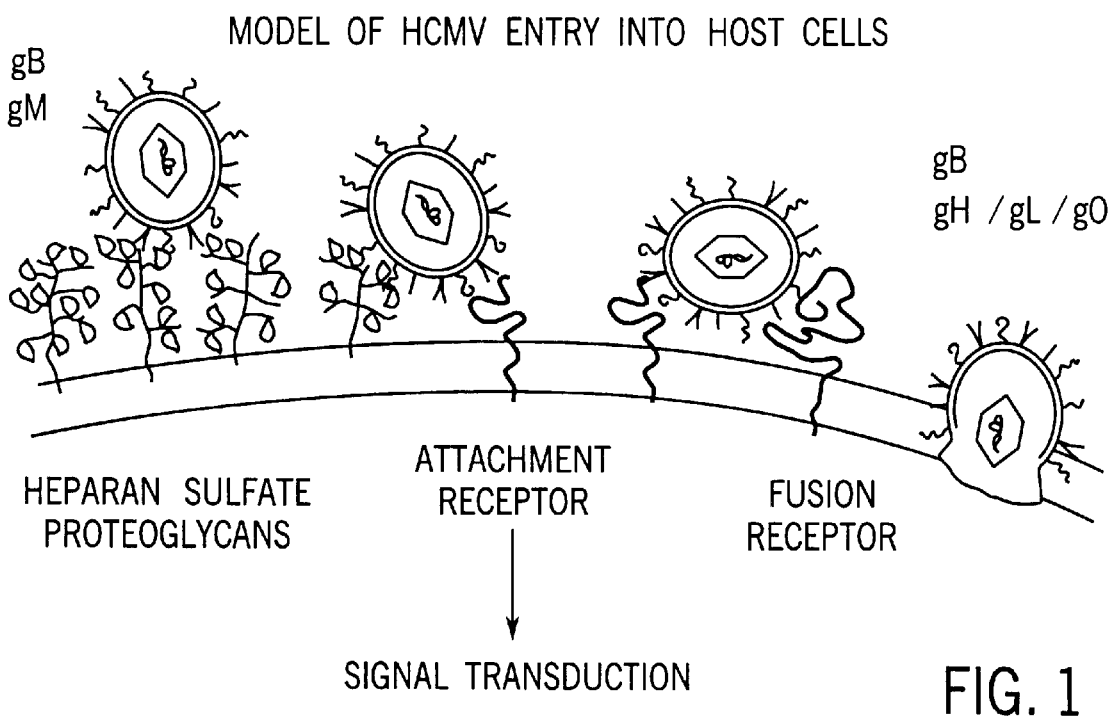
FIG. 1 is a diagram of HCMV entry into human fibroblasts. HCMV enters human fibroblasts by direct, pH-independent fusion of ther viral envelope with the host cell membrane. Initial attachment occurs by binding of viral envelope glycoprotein B to heparan sulfate proteoglycans. This low-affinity attachment is followed by high affinity attachment of gB to an unidentified receptor. Finally, in a step which depends on a viral glycoprotein complex of gH, gL, and gO, the lipid bilayers fuse and the nucleocapsid is released into the cytoplasm.

FIG. 1 is a diagram of HCMV entry into human fibroblasts. HCMV enters human fibroblasts by direct, pH-independent fusion of ther viral envelope with the host cell membrane. Initial attachment occurs by binding of viral envelope glycoprotein B to heparan sulfate proteoglycans. This low-affinity attachment is followed by high affinity attachment of gB to an unidentified receptor. Finally, in a step which depends on a viral glycoprotein complex of gH, gL, and gO, the lipid bilayers fuse and the nucleocapsid is released into the cytoplasm.

Figure 2:
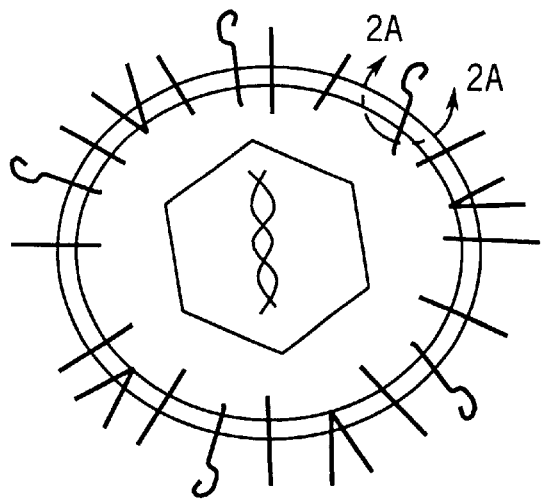
FIG. 2 is a model of the tripartite gCIII complex in the HCMV envelope. gH is an 86 kD glycoprotein with a C-terminal membrane anchor domain. It is disulfide bonded to gL, which is a 34 kD protein with no predicted transmembrane domains. Attached to this complex is a third protein, gO, which is highly glycosylated and appears as a diffuse band of approximately 125 kD on SDS-PAGE. The disulfide bond structure of this complex is not known, and the membrane orientation of gO has not been characterized.
Figure 2A:
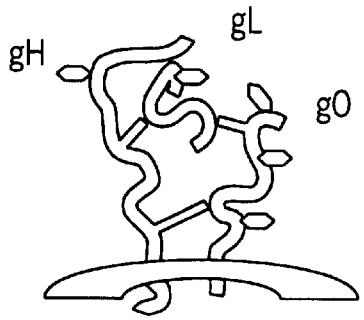
FIG. 2A is an expanded view of a segment of FIG. 2.

FIG. 2 is a model of the tripartite gCIII complex in the HCMV envelope. gH is an 86 kD glycoprotein with a C-terminal membrane anchor domain. It is disulfide bonded to gL, which is a 34 kD protein with no predicted transmembrane domains. Attached to this complex is a third protein, gO, which is highly glycosylated and appears as a diffuse band of approximately 125 kD on SDS-PAGE. The disulfide bond structure of this complex is not known, and the membrane orientation of gO has not been characterized. FIG. 2A is an expanded view of a segment of FIG. 2.

The sections below describe various embodiments of our invention. These embodiments all require an understanding of the characteristics of gO. One of skill in the art would be able to review *Journal of Virology* 72(10):P8191 –P8197 (1988) and *Journal of Virology* 71 (7):5391–5398 (1997) to understand the location and characteristic of gene-encoding gO and the protein itself. Both of these articles are incorporated by reference as if fully set forth herein. Additionally, FIG. 3 is the predicted amino acid sequence of gO. The predicted signal/anchor domain is bolded and potential N-glycosylation sites are underlined. Kyte-Doolittle hydropathy analysis is shown in the bottom panel.

In brief, one skilled in the art could obtain the gene encoding gO (UL74) from human cytomegalovirus by standard recombinant DNA technologies including direct restriction isolation of the DNA segment containing the UL74 gene region or by DNA amplification technologies employing oligonucleotide primers based on the published cytomegalovirus genomic sequence (Chee, M. S., et al., *Curr. Top. Microbiol. Immunol.* 154(125):125–169) With the UL74 gene in hand, one skilled in the art could use standard protein production technology to produce the gO protein.

B. Glycoprotein O as a new anti-CMV drug target.

Entry of CMV into susceptible cells involves sequential, perhaps cooperative interactions between distinct viral envelope glycoprotein complexes and cellular molecules that serve as receptors for the virus (Compton, T, Scand. *J. Infect. Dis.* 99:30–32,1995; Compton, T., et al., *Virology* 193(2):834–841,1993). The culmination of these virus-cell interactions is fusion between the virus envelope and the cell plasma membrane (Compton, T., et al., *Virology* 191(1):387–395, 1992). Compounds that impede the entry pathway would successfully block virus infection and may also prevent the virus from establishing the lifelong latent infection.

For example, we have shown that a purified soluble form of another CMV glycoprotein, glycoprotein B (gB) (Carlson, C., et al., *Virology* 239:198–205,1997) blocks CMV infection by occupying gB-binding sites that need to be utilized by the virus in order to initiate infection (Boyle, K. A. and T. Compton, *J. Virol.* 72:1826–33,1998). The gO protein may have a cellular receptor or undergo conformational changes needed to mediate virus-cell fusion. We have already produced soluble forms of gO in a manner similar to that of gB. This reagent will allow us to determine if gO has a cellular receptor. If so, test compounds may be generated by rational design or random screening that would be an effective anti-CMV therapies. For example, we predict that soluble or purified CMV glycoprotein O or fragments of glycoprotein O are suitable inhibitors.

Alternatively, rational design based on the gO fusion mechanism or random screening of compounds may reveal compounds that are very efficient antiviral drugs. These compounds may be highly specific for CMV and potentially circumvent cellular toxicity problems that compromise current anti-CMV drugs.

Therefore, in one embodiment, the present invention is a method of evaluating candidate compounds as new anti-CMV drugs using glycoprotein O as a drug target. In one version of this embodiment, one would design an anti-CMV drug by evaluating the gO/gO receptor interaction and designing a drug that will mimic the action of gO, thus outcompeting the gO-containing complex and preventing CMV infection.

One would screen these candidate drugs in a model CMV infection system. For example, using the sensitive virus entry assay referred to above (Pietropaolo, R. and T. Compton, supra, 1997, incorporated by reference), compounds will be screened for their ability to inhibit CMV entry and initiation of infections. Compounds will also be tested in assays designed to measure membrane fusion, preferably at both the level of virus-cell and cell-to-cell spread of infection. Compounds which reduce or abolish fusion, entry and spread of infection would be considered highly valuable candidates for further analysis such as pharmacokinetics and bioviability.

We have now developed a rapid, sensitive, improved method to study human cytomegalovirus (HCMV) ligand/receptor interactions and HCMV mediated fusion with susceptible host cells. Earlier assays relied on HCMV infection and expression of the major immediate early protein as an indicator of infection. One limitation of conducting structure function analysis of specific viral glycoproteins and, in particular, the analysis of potential inhibitory compounds is that fact that composition of the HCMV envelope is incompletely defined. Thus, specificity is very difficulty to definitively establish. To circumvent this lack of knowledge, we have developed a pseudotyping system in which we can display single or combinations of HCMV envelope proteins. The system is based on a very simple enveloped virus, vesicular stomatitis virus (VSV) which encodes a single glycoprotein and is capable of promiscuously incorporating foreign viral envelope proteins. We employed a recombinant VSV strain that has its single glycoprotein gene, G, deleted. Substituted in place of G is the gene encoding green fluorescent protein (GFP) (Takada, A., et al., *Proc. Natl. Acad. Sci. USA* 94:14764–14769, 1997) When the recombinant VSV virus is introduced into cells along with a mammalian expression plasmid encoding an HCMV envelope glycoprotein, VSV particles are produced that contain that HCMV envelope glycoprotein in the VSV envelope. Proof of principal has been established with the HCMV glycoprotein B as well as gH/gL. Thus, precise combinations of HCMV envelope proteins can be displayed in the VSV pseudotypes and functionally tested for binding and fusion activity. Entry is easily monitored by GPF expression. Pseudotypes displaying gO and gO/gH/gL can be produced and compounds that interfere with gO binding to potential receptors can easily identified.

Candidate compounds would be evaluated for their ability to block cytomegalovirus entry by analyzing the inhibition of expression of the major immediate early protein of HCMV as described in Pietropaolo and Compton, (1997, supra) or by plaque inhibition assays. Such compounds might also be expected to interfere with cell to cell spread resulting in a small plaque phenotype.

In another embodiment of the present invention, one would design a drug screen by determining whether a candidate drug can outcompete or interfere with the go-containing complex in a model system.

Candidate compounds could be evaluated for their ability to block gO in the pseudotyping model system described above. Pseudotypes displaying gO in conjunction with its partners, gH and gL would be incubated with candidate compounds. Inhibition would be determined by lack of GFP expression compared to untreated controls.

Candidate compounds could be evaluated for their ability to block or outcompete with gO binding to cells by direct binding assay with recombinant gO protein.

C. Glycoprotein O as a subunit vaccine.

To date, only varicella zoster virus, a human herpesvirus and the causative agent of childhood chicken pox and an adult reactive disease known as zoster or "shingles", has an efficacious vaccine. Given the ability of herpes viruses to establish an incurable latent infection, vaccines composed of live, or attenuated virus strains, are problematic due to the possibility of reactivation of the latent virus. Thus the trend in the field has been towards the identification of appropriate individual components or mixtures of viral components produced from recombinant sources. These components would need to elicit the production of antibodies that prevent or neutralize infection. Generally subunit vaccine components are purified, recombinant forms of the identified target. We have shown that antibodies to gO block CMV entry into cells and thereby prevent infection which suggest gO may serve either individually as a single subunit vaccine component or as a component of a cocktail of subunits.

Commonly, subunit vaccine components derived from transmembrane proteins such as gO are engineered to lack the membrane anchoring region and cytoplasmic portions. We have recently shown that gO is a type II membrane protein with its carboxyl terminus oriented extracellularly and its amino terminus in the cytoplasm (unpublished results). Thus, a soluble form of gO would likely consist of amino acids 31–466. We envision that other smaller forms also lacking the membrane spanning domain (a.a. 14–31) will also be suitable.

To accomplish the development of the vaccine, one would engineer the desired soluble form by standard mutagenesis and express the soluble gO in a suitable protein expression system, such as baculovirus expression or stably-transfected mammalian cell lines. Purified soluble protein would be used in efficacy testing by (a) does soluble gO elicit neutralizing antibodies, and (b) do these antibodies protect in model challenge experiments. Although there is no animal model for human cytomegalovirus, there is a gO equivalent in mouse cytomegalovirus (Huber, M. T. and T. Compton, supra, 1998) which would be appropriate.

D. Diminishing CMV Infection

In another embodiment, the present invention is a method of diminishing CMV infection comprising the step of introducing anti-CMV gO antibodies into a CMV infected subject.

As mentioned in the background of the invention, HCMV is a significant opportunistic pathogen in various clinical settings such as neonates and infants, persons with AIDS and recipients of organ and bone marrow transplants. CMV can reside in virtually every organ in the body and be transmitted with transplanted organ tissue. Spread of infection is frequently between lymphoid cells that harbor virus and the endothelial cells of the vascular tissues. The endothelial cells, in particular, are a critical conduit between the infected blood cells and underlying organ tissue. Also as mentioned, there is no animal model for HCMV infection. In the laboratory most studies are conducted in human fibroblasts cells that while very useful are not highly targeted cell types in in vivo.

We have established biologically targeted cell types in the laboratory and have the capability to study transmission between these cells types. Specifically, we can culture human microvascular and macrovascular (aortic) endothelial cell cultures. These cell cultures can be infected with HCMV and monitored for spread both between neighboring endothelial cells and for spread between added human lymphoid cells. This represents a tremendous advantage to evaluate anti gO compounds that impede the spread of infection from cell to cell. Blocking cell to cell spread is likely the key to diminish HCMV infections in patients with active HCMV disease.

Specifically, anti-CMV gO antibodies could be tested for their ability to interfere with transmission of infected endothelial cells to lymphoid cells added to the culture. The reciprocal experiment could also be performed. Transmission of CMV to uninfected cells could be monitored by transfer of CMV proteins such as the capsid protein or the major tegument protein or by expression of the major immediate early protein as described above. Compounds and antibodies could be identified that interfere with this process.

In another embodiment, the present invention is also an anti-CMV gO antibody. The anti-CMV gO antibody was described in Huber and Compton, *J. Virol.* 72:8191–8197, 1998. The antibody is a polyclonal serum produced in rabbits.

We claim:

1. A method of screening candidate anti-CMV drugs for the ability to block CMV entry into a host cell comprising the step of determining whether a candidate drug interferes with glycoprotein O binding to glycoprotein O receptor wherein glycoprotein O is within a complex with glycoprotein H and glycoprotein L.

2. The method of claim 1 wherein candidate drugs are additionally evaluated for their ability to block CMV entry into a host cell.

3. The method of claim 2, wherein the evaluation comprises analyzing the inhibition of the major early protein of HCMV.

* * * * *

SEQUENCE LISTING

<160> NUMBER OF SEQ ID NOS: 1

<210> SEQ ID NO 1
<211> LENGTH: 465
<212> TYPE: PRT
<213> ORGANISM: Human cytomegalovirus

<400> SEQUENCE: 1

```
Met Gly Arg Lys Glu Met Met Val Arg Asp Val Pro Lys Met Phe Val
 1               5                  10                  15

Leu Ile Ser Ile Ser Phe Leu Leu Val Ser Phe Ile Asn Cys Lys Val
            20                  25                  30

Met Ser Lys Ala Leu Tyr Asn Arg Pro Trp Arg Gly Leu Val Leu Ser
        35                  40                  45

Lys Ile Gly Lys Tyr Lys Leu Asp Gln Leu Lys Leu Glu Ile Leu Arg
    50                  55                  60

Gln Leu Glu Thr Thr Ile Ser Thr Lys Tyr Asn Val Ser Lys Gln Pro
65                  70                  75                  80

Val Lys Asn Leu Thr Met Asn Thr Glu Phe Pro Gln Tyr Tyr Ile Leu
                85                  90                  95

Ala Gly Pro Ile Gln Asn Tyr Ser Ile Thr Tyr Leu Trp Phe Asp Phe
            100                 105                 110

Tyr Ser Thr Gln Leu Arg Lys Pro Ala Lys Tyr Val Tyr Ser Gln Tyr
        115                 120                 125

Asn His Thr Ala Lys Thr Ile Thr Phe Arg Pro Pro Pro Cys Gly
    130                 135                 140

Arg Val Pro Ser Met Thr Cys Leu Ser Glu Met Leu Asn Val Ser Lys
145                 150                 155                 160

Arg Asn Asp Thr Gly Glu Gln Gly Cys Gly Asn Phe Thr Thr Phe Asn
                165                 170                 175

Pro Met Phe Phe Asn Val Pro Arg Trp Asn Thr Lys Leu Tyr Val Gly
            180                 185                 190

Pro Thr Lys Val Asn Val Asp Ser Gln Thr Ile Tyr Phe Leu Gly Leu
        195                 200                 205

Thr Ala Leu Leu Leu Arg Tyr Ala Gln Arg Asn Cys Thr His Ser Phe
    210                 215                 220

Tyr Leu Val Asn Ala Met Ser Arg Asn Leu Phe Arg Val Pro Lys Tyr
225                 230                 235                 240

Ile Asn Gly Thr Lys Leu Lys Asn Thr Met Arg Lys Leu Lys Arg Lys
                245                 250                 255

Gln Ala Pro Val Lys Glu Gln Phe Glu Lys Ala Lys Lys Thr Gln
            260                 265                 270

Ser Thr Thr Thr Pro Tyr Phe Ser Tyr Thr Thr Ser Ala Ala Leu Asn
        275                 280                 285

Val Thr Thr Asn Val Thr Tyr Ser Ile Thr Thr Ala Ala Arg Arg Val
    290                 295                 300

Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Gln Asn Pro Phe Cys Glu Pro Ser Thr Asn Arg Thr Ala
            340                 345                 350

Val Ser Glu Phe Met Lys Asn Thr His Val Leu Ile Arg Asn Glu Thr
```

-continued

```
                       355                       360                           365

Pro Tyr Thr Ile Tyr Gly Thr Leu Asp Met Ser Ser Leu Tyr Tyr Asn
    370                     375                 380

Glu Thr Met Phe Val Glu Asn Lys Thr Ala Ser Asp Ser Asn Lys Thr
385                     390                 395                     400

Thr Pro Thr Ser Pro Ser Met Gly Phe Gln Arg Thr Phe Ile Asp Pro
                405                     410                 415

Leu Trp Asp Tyr Leu Asp Ser Leu Leu Phe Leu Asp Glu Ile Arg Asn
            420                     425                 430

Phe Ser Leu Arg Ser Pro Thr Tyr Val Asn Leu Thr Pro Pro Glu His
        435                 440                 445

Arg Arg Ala Val Asn Leu Ser Thr Ser Asn Ser Leu Trp Trp Trp Leu
    450                     455                 460

Gln
465
```